(12) United States Patent
Gnoth et al.

(10) Patent No.: US 9,936,987 B2
(45) Date of Patent: Apr. 10, 2018

(54) LOCKING SLEEVE FOR A PEDICLE SCREW

(71) Applicant: Aesculap AG, Tuttlingen (DE)

(72) Inventors: Barbara Gnoth, Immendingen (DE); Denis Ricci, Tuttlingen (DE); Janina Ackermann, Tuttlingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/867,172

(22) Filed: Sep. 28, 2015

(65) Prior Publication Data

US 2016/0095635 A1 Apr. 7, 2016

(30) Foreign Application Priority Data

Oct. 7, 2014 (DE) ........................ 10 2014 114 530

(51) Int. Cl.
*A61B 17/70* (2006.01)
*A61B 90/00* (2016.01)

(52) U.S. Cl.
CPC ........ *A61B 17/7091* (2013.01); *A61B 17/708* (2013.01); *A61B 17/7032* (2013.01); *A61B 17/7083* (2013.01); *A61B 17/7085* (2013.01); *A61B 2090/037* (2016.02)

(58) Field of Classification Search
CPC .............. A61B 17/708; A61B 17/7083; A61B 17/7085; A61B 17/7091; A61B 2017/681
See application file for complete search history.

(56) References Cited

U.S. PATENT DOCUMENTS

| | | | |
|---|---|---|---|
| 8,496,661 B2 | 7/2013 | Moore | |
| 2007/0270813 A1* | 11/2007 | Garamszegi | A61B 17/7032 606/278 |
| 2008/0077135 A1* | 3/2008 | Stad | A61B 17/8875 606/86 A |
| 2009/0099605 A1 | 4/2009 | Fallin | |
| 2011/0196426 A1* | 8/2011 | Peukert | A61B 17/7083 606/279 |
| 2012/0271365 A1* | 10/2012 | Daubs | A61B 17/7086 606/86 A |
| 2012/0323278 A1 | 12/2012 | Tsuang | |
| 2013/0096635 A1* | 4/2013 | Wall | A61B 17/7085 606/305 |
| 2014/0277206 A1* | 9/2014 | Reitblat | A61B 17/7085 606/86 A |

FOREIGN PATENT DOCUMENTS

| | | |
|---|---|---|
| DE | 102011111403 | 10/2012 |
| EP | 2777573 | 9/2014 |

OTHER PUBLICATIONS

European Search Report dated Feb. 11, 2016 for European Application No. 15186068.1 with translation.
German Search Report dated May 15, 2015 for German Application No. 10 2014 114 530.5, including partial translation.

* cited by examiner

*Primary Examiner* — Julianna N Harvey
(74) *Attorney, Agent, or Firm* — RatnerPrestia

(57) ABSTRACT

A locking sleeve for receiving and locking the legs of a pedicle screw includes a stop ring provided on an inner side of a locking sleeve and resting on an upper edge of the legs, limiting the accommodation depth of the legs in the locking sleeve, and a plurality of groove blocks on the inner side of the locking sleeve which can be inserted between the legs of the pedicle screw for defining a fixed distance between the legs.

9 Claims, 5 Drawing Sheets

LOCKING SLEEVE FOR A PEDICLE SCREW

RELATED APPLICATION

This application claims the benefit of priority under 35 U.S.C. § 119 of German Application No. DE 10 2014 114 530.5, filed Oct. 7, 2014, the content of which is incorporated by reference in its entirety and for all purposes.

FIELD

The present invention relates to a locking or securing sleeve for receiving and locking/securing the extended legs or break-off legs of a pedicle screw.

BACKGROUND

In minimally invasive spinal surgery, pedicle screws comprising extended legs offer the possibility—especially in vertebral repositioning—to be able to do without various instruments and thus result in a significantly smaller incision in the skin. This allows to reduce the stressing of the patient during the operation and to accelerate the healing after the operation. In vertebral repositioning, tulip head pedicle screws comprising extended legs are screwed into the vertebral pedicles first; after this, an alignment rod is inserted into the tulip heads of several pedicle screws for mutually aligning the pedicle screws. If the pedicle screws have been placed in the vertebral pedicles at the desired positions and correctly aligned, the surgeon breaks off the extended legs of the pedicle screws or its tulip heads. In order to facilitate this procedure and allow for breaking the legs in a burr-free manner, pedicle screws comprising extended legs each comprise a predetermined breaking point between the screw head and the legs.

The extended legs increase the load on the predetermined breaking point as a result of deformation forces which are caused by tissue stresses and the manipulation on the part of the surgeon. This is why the position of the legs has to be secured in order to prevent the legs from breaking off too early.

To this end, locking rings or locking sleeves are known which can be slipped over the extended legs of a pedicle screw to stabilize the legs during inserting and aligning the pedicle screw.

A simple leg protection sleeve in the form a simple ring which can be slipped over the legs of a pedicle screw, is known from DE102011111403A1, for example. The inner radius of this leg protection sleeve corresponds to the outer radius of the tulip head of the pedicle screw and the inner circumferential surface of the leg protection sleeve is formed to be smooth. The disadvantage of this solution is that the position of the legs within the leg protection sleeve is not determinedly defined as the legs can move along the smooth inner circumferential surface of the leg protection sleeve in uncontrollable manner. Moreover, the accommodation depth of the legs in the leg protection sleeve is not defined either and the leg protection sleeve can get out of place along the axial direction of the legs, which is undesired.

In addition, the leg protection sleeve does not have any other function apart from stabilizing the legs; thus, the process of aligning several pedicle screws is performed in each case with one such leg protection sleeve by inserting a correction rod in the respective tulip heads of the pedicle screws. This has the effect that the correction rod is very close to the tissue of the patient and any possible deformation of the correction rod by the surgeon may lead to an unnecessary damage of the tissue.

A somewhat better defined way of positioning the legs in the locking ring is offered by a locking ring which is commonly known from the prior art, in particular by the locking ring known from US20130096635A1.

The commonly known locking ring is a half ring comprising two mounting openings or separate channels for the two legs of a pedicle screw. This locking ring can be slipped over the legs of a pedicle screw, too, but threading the legs into the respective mounting opening is time-consuming and difficult. Also with the commonly known locking ring, the accommodation depth of the legs in the leg protection sleeve is not defined and the locking ring may undesirably slip along the axial direction of the legs. Apart from the stabilization of the legs, the commonly known ring does not fulfil further functions and the previously described difficulty with inserting a correction rod in the tulip heads of the pedicle screws during their mutual alignment remains. What is more, the passage between the legs which is available for instrument access and defined by the legs is narrowed, as the mounting openings entirely enclose the legs. This makes it more difficult for the surgeon to position the pedicle screws, as the access channel between the legs is narrowed by the ring.

The locking ring according to US20130096635A1 also comprises two mounting openings for the two legs of a pedicle screw. In order to keep the legs in position and prevent an undesired movement of the legs, the mounting openings enclose the legs with very small clearance. This is why threading the legs into the respective mounting opening is here very time-consuming and difficult, too.

At its end facing away from the pedicle screw, the locking ring has a stopping piece in each of the mounting openings, which limits and defines the accommodation depth of the legs in the locking ring. In order to prevent an undesired slipping of the locking sleeve from the legs, each mounting opening additionally comprises a narrow groove in which a corresponding groove block of an extended leg is placed if the leg is inserted in the mounting opening. For releasing such anchoring and removing the locking ring from the legs of the pedicle screw, the locking ring has provided its outer side with an elastically deformable pressure arm adjacent to a groove, and the surgeon can apply an external pressure on said pressure arm whereby the latter moves into the groove, pushes the groove block out of the groove and thus separates the leg from the locking ring.

This locking ring admittedly offers a safe and defined positioning of the legs of a pedicle screw in the locking ring, but the design of the locking ring comprising several stopping pieces, narrow mounting openings, narrow grooves and pressure arms results in too many undercuts and blind areas where dirt or tissue particles arising during operation may accumulate. The cleaning of a locking ring having such a complex design is very time-consuming and difficult.

Apart from the stabilization of the legs, the locking ring known from US20130096635A1 does not fulfil any further functions and the problem of damaging the tissue during inserting a correction rod in the tulip heads of the pedicle screws during their mutual alignment remains also in this case. The inner diameter of the passage between the legs (which is available for instrument access and defined by the legs) is also reduced, as the mounting openings enclose the legs at least in part, and the positioning of the pedicle screws is more difficult for the surgeon.

In order to avoid the problems related to the reduction of the inner diameter of the instrument-accessible access between the legs, it is possible to equip the instrument itself (e.g. a screwdriver) with a locking ring, as is known for instance from U.S. Pat. No. 8,496,661B2. In this arrangement, the locking ring is formed in one piece with the screwdriver, so that the legs will move at the same time and corresponding to the rotation of the screwdriver. This avoids any shearing effect on the extended legs.

The disadvantage is that the instrument connected with the locking ring in one piece can only be used for those screws for which the locking ring is suitable. Here, the problem of damaging the tissue during inserting a correction rod in the tulip heads of the pedicle screws during their mutual alignment exists as well.

SUMMARY

The present invention is based on the object to provide a locking sleeve which allows a defined positioning of the legs of a pedicle screw in the locking sleeve without narrowing the instrument-accessible access between the legs and which can be easily cleaned, too.

This object is achieved by the locking sleeve comprising the features described herein.

The central idea of the present invention is, instead of providing the locking/securing sleeve with mounting openings each enclosing the legs of the pedicle screw at least in part, to provide it with a number of slotnuts/groove blocks/protrusions on the inner side of the locking/securing sleeve which are adapted to be able to be placed/inserted between the legs and keep the legs in a fixed defined distance relative to each other. As the groove blocks/slotnuts are only placed/inserted between the legs without enclosing them, the passage/inner cross-section between the legs is not narrowed by the locking/securing sleeve. In order to define the accommodation depth of the legs in the locking/securing sleeve, the locking/securing sleeve has preferably its inner side provided with a stop ring or axial stop in the form of a protrusion extending radially inwards, which is provided to rest on the upper edge of the legs (distale front edge). Due to the simple configuration of the locking/securing sleeve comprising the stop ring and the number of groove blocks/slotnuts, the legs of a pedicle screw can be reliably fixed in a defined axial and/or rotary position in the locking/securing sleeve without creating many dead areas or undercuts and thus disadvantages as seen from the perspective of hygiene.

In order to simplify the process of placing the locking/securing sleeve on the legs, one embodiment makes provision that at least one of the number of groove blocks/slotnuts on the inner side of the locking/securing sleeve tapers in conical fashion (i.e. preferably in V-shaped manner) contrary to the direction of inserting the legs of the pedicle screw in the locking/securing sleeve. Here, the groove blocks/slotnuts are inserted in the slot/gap between the legs of the pedicle screw/tulip head. Owing to the conical shape, the legs are kept spaced from each other with maximum distance.

The stop ring/axial stop serves to axially limit the accommodation depth of the legs of the pedicle screw into the locking/securing sleeve. The stop ring/axial stop is a preferably annular protrusion on the inner side of the locking/securing sleeve, which extends along the entire circumferential line of the locking/securing sleeve or over a part of it. It is preferred that the stop ring/axial stop is formed near the end of the locking/securing sleeve remote from the pedicle screw. In order to ensure that the passage formed between the legs of the pedicle screw is not constricted by the stop ring/axial stop, a preferred embodiment makes provision that the radial extension of the stop ring/axial stop into the inner circumference of the locking/securing sleeve is limited by the inner circumference of the passage defined by the legs of the pedicle screw. This means that the stop ring/axial stop does not protrude radially inwards beyond the legs into the passage formed between the legs and hence does not impede the process of inserting instruments into the passage.

In a further preferred embodiment, the radial extension of the number of groove blocks/slotnuts into the inner circumference of the locking/securing sleeve corresponds at most to the radial extension of the stop ring/axial stop into the inner circumference of the locking/securing sleeve. This prevents the groove blocks/slotnuts from narrowing the passage formed between the legs.

The locking/securing sleeve can be further improved in that at least one alignment groove/double groove is provided on the end of the locking/securing sleeve facing away from the pedicle screw and serves for transversely receiving a correction rod for aligning the legs of several pedicle screws with respect to one another. This allows to use the locking/securing sleeve itself for the alignment of several pedicle screws by means of a correction rod. Here, the correction rod is inserted in the alignment grooves of several locking/securing sleeves transverse to the sleeve axis. This means that the correction rod will not be located directly next to the tissue of the patient, as is the case with the commonly known prior art alignment of the pedicle screws by inserting a correction rod in the tulip heads/between the legs of the pedicle screws. Thus, the risk of damaging the tissue due to a bending of the correction rod directly next to the patient tissue is reduced and the alignment becomes less invasive. What is more, the legs are stressed to a lesser extent (because they are not bent up with respect to each other) and hence their predetermined breaking points are not broken.

In an advantageous embodiment, the at least one alignment groove on the locking/securing sleeve is in alignment with at least one of the groove blocks/slotnuts. By this means, a movement of the alignment groove by the correction rod during aligning the pedicle screws is transferred in optimum fashion to the legs of the pedicle screw.

According to an advantageous further development, the locking/securing sleeve further comprises at least one restraining element on the end of the locking/securing sleeve near the pedicle screw for preventing an undesired stripping of the locking/securing sleeve from the legs contrary to and/or in the direction of inserting the legs into the locking/securing sleeve. According to one embodiment, the at least one restraining element is formed as an elastically deformable latching arm (a spring tongue comprising a terminal latching nose), preventing a movement of a leg contrary to and/or in the direction of inserting the leg in the locking/securing sleeve by latching in place in a corresponding elongated hole in the leg. Here, the radial extension of the at least one latching arm or its latching nose into the inner circumference of the locking/securing sleeve corresponds at most to the radial extension of the stop ring/axial stop into the inner circumference of the locking/securing sleeve. This prevents the at least one latching arm from narrowing the passage formed between the legs.

In a preferred embodiment, the locking/securing sleeve consists of two half sleeves which are firmly connected to each other according to the press button principle by the number of groove blocks/slotnuts on the inner side of the locking/securing sleeve and a corresponding number of corresponding mating blocks on the outer side of the locking/securing sleeve. As an alternative, the locking/securing sleeve may also be manufactured in one piece or the half sleeves can be connected in any other way. The locking/securing sleeve can be made of metal or plastics or any other advantageous material.

In order to improve the stability of the locking/securing sleeve, the locking/securing sleeve may have its outer side additionally provided with several stiffening flutes extending along the longitudinal axis of the locking/securing sleeve.

DESCRIPTION OF THE FIGURES

Further features and advantages of the present invention will be apparent from the following description of preferred embodiments with reference to FIGS. 1 to 9 in which.

DETAILED DESCRIPTION

Figure 1:
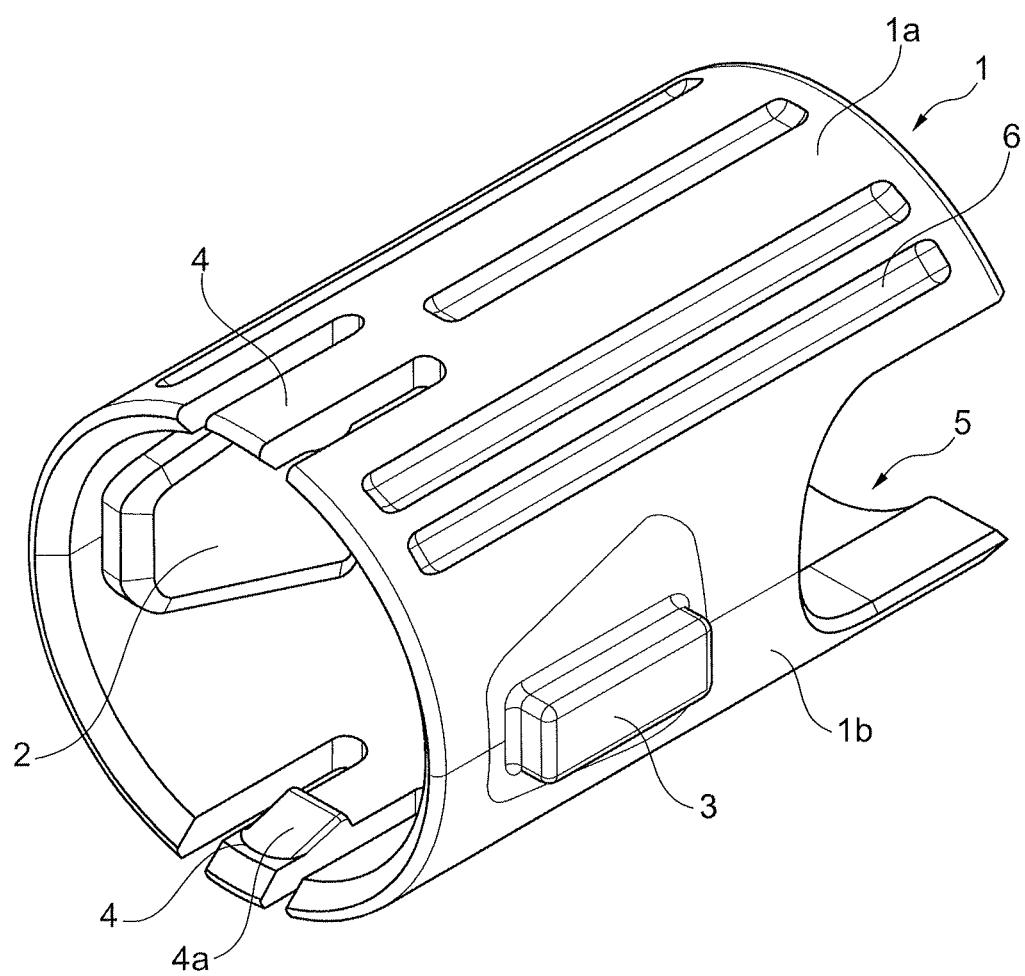
FIG. 1 is a side view of a locking/securing sleeve according to the invention.

As shown in FIG. 1, the locking sleeve 1 is composed of two identical half sleeves 1a, 1b which are connected to each other according to the press button principle by means of two axially conical groove blocks 2 on the inner side of the locking sleeve 1 and two corresponding mating blocks 3 on the outer side of the locking sleeve 1. In this arrangement, one groove block 2 and one mating block 3 on the inner respectively outer side of the locking sleeve 1 are opposite each other. The two conical groove blocks on the inner side of the locking sleeve 1 taper toward a first end of the locking sleeve 1 contrary to the direction of inserting the legs of a commonly known pedicle screw according to the initially mentioned prior art into the locking sleeve 1. For preventing the locking sleeve 1 from slipping off the legs of the pedicle screw contrary to and/or in the direction of inserting the legs of the pedicle screw into the locking sleeve 1, the locking sleeve 1 has its first end provided with two elastically deformable, axially extending latching arms or spring tongues 4. Each latching arm 4 comprises a protrusion or latching nose 4a which protrudes inwards into the inner circumference of the locking sleeve 1 and is flattened in wedge-shaped fashion toward the first end of the locking sleeve 1. At a second end opposite to the first end of the locking sleeve 1, the locking sleeve 1 comprises two axially extending alignment grooves 5 (only one can be seen in FIG. 1) which each are in axial alignment with one of the diametrically opposite conical groove blocks 2 and in which a correction rod (see FIG. 9) for mutually aligning several locking sleeves 1 can be placed so as to lie transverse to the sleeve 1. The outer side of the locking sleeve 1 is additionally provided with several axial stiffening flutes 6.

Figure 2:
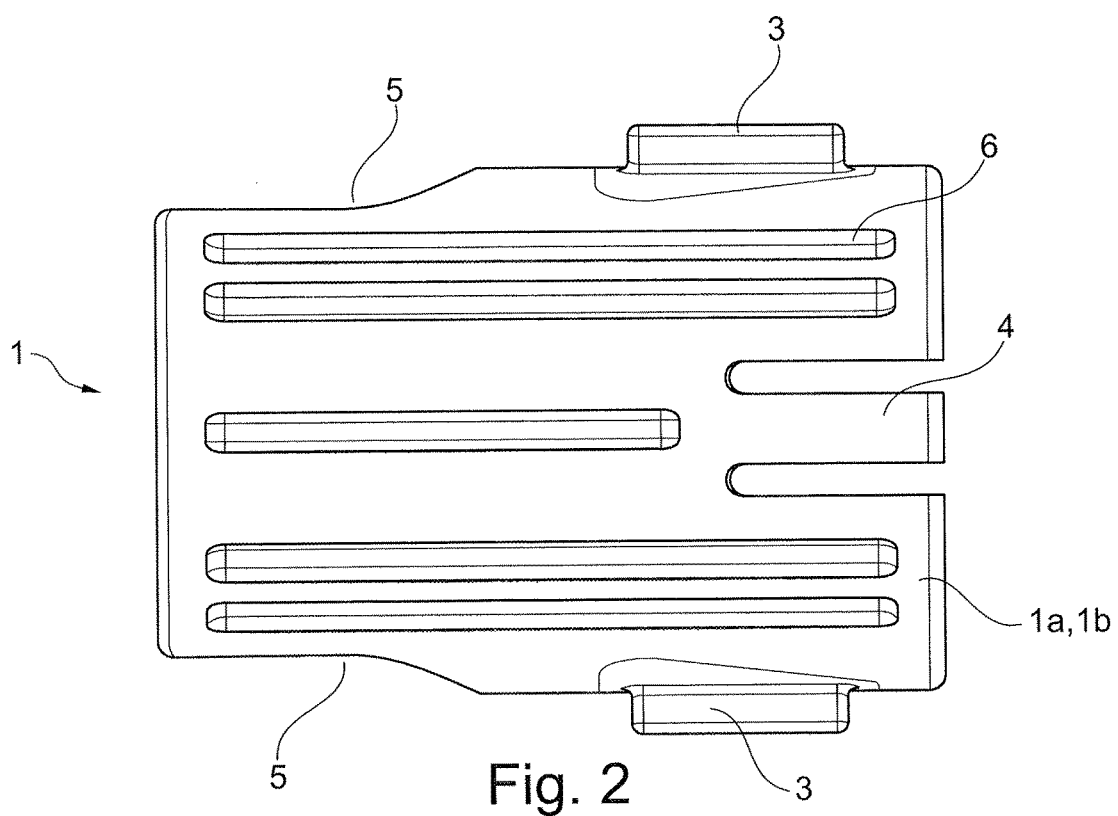
FIG. 2 is a side view of a locking/securing sleeve according to the invention, seen from another point of view than that in FIG. 1.

FIG. 2 shows the locking sleeve of FIG. 1 in a side view and as seen from another point of view than in FIG. 1. In this illustration, only one of the two half sleeves 1a and 1b can be seen. The same reference symbols relate to the same components here. As can be taken from this Figure, the spring tongue/the latching arm 4 is formed by two circumferentially spaced axial slots which end approximately at ⅓ of the sleeve length.

Figure 3:
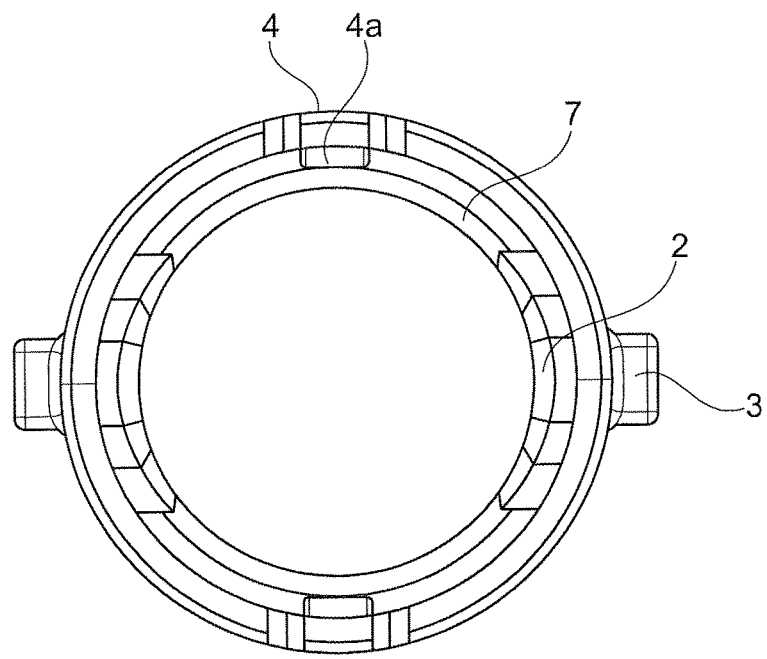
FIG. 3 is a front view of a locking/securing sleeve according to the invention.

FIG. 3 shows a cross-sectional view/front view of the locking sleeve 1 according to the invention, with the first end of the locking sleeve 1 facing the viewer. The same reference symbols refer to the same components, as in the preceding Figures. In this view, an annular stop ring 7 can also be seen which is formed along the entire inner circumferential line of the locking sleeve 1 and radially protrudes into the inner circumference of the locking sleeve 1. Further, one can see that the groove blocks 2 and latching arms 4 in radial inward direction do not protrude into the inner circumference of the locking sleeve defined by the stop ring 7. This is why the inner diameter of the locking sleeve 1 and hence the instrument-accessible passage between the legs of the pedicle screw is not narrowed.

Figure 4:
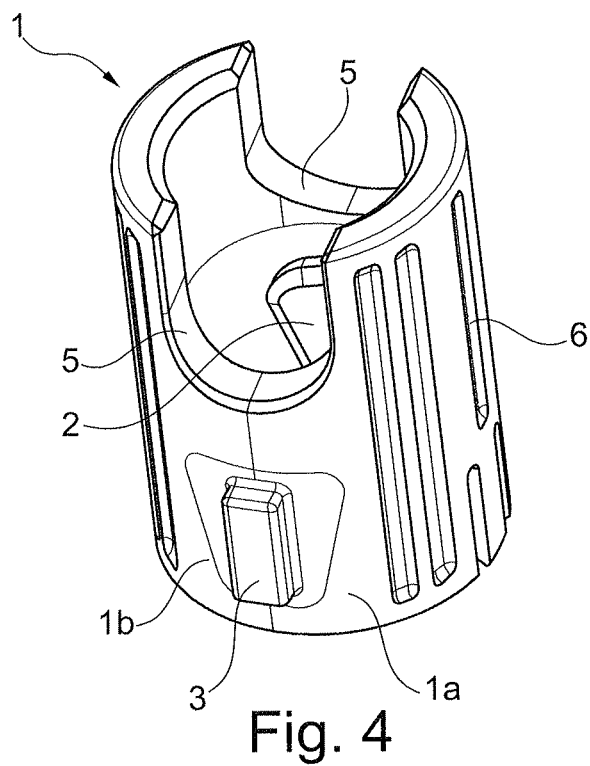
FIG. 4 is a lateral top view of a locking/securing sleeve according to the invention.

FIG. 4 clearly shows the two alignment grooves 5 on the second end of the locking sleeve 1. Each of these alignment grooves 5 is in axial alignment with a respective groove block 2.

Figure 5:
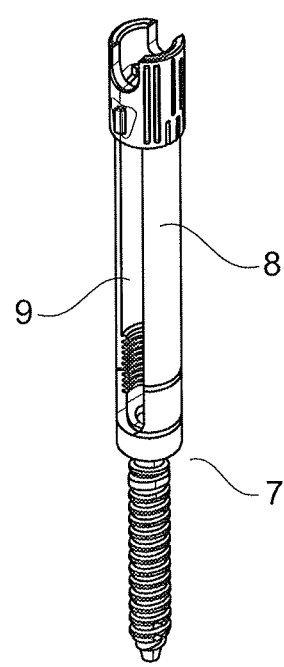
FIG. 5 shows a pedicle screw comprising extended legs which have a locking/securing sleeve according to the invention placed thereon.

FIG. 5 shows a pedicle screw 7 comprising extended legs 8 on which a locking sleeve 1 according to the invention is placed. The two extended legs 8 of the pedicle screw 7 form the instrument-accessible passage 9 between them. The groove blocks 2 of the locking sleeve 1 keep the legs 8 at the maximum distance from each other to achieve the maximum diameter of the passage 9 and hence an easy insertion of instruments into the passage 9.

Figure 6:
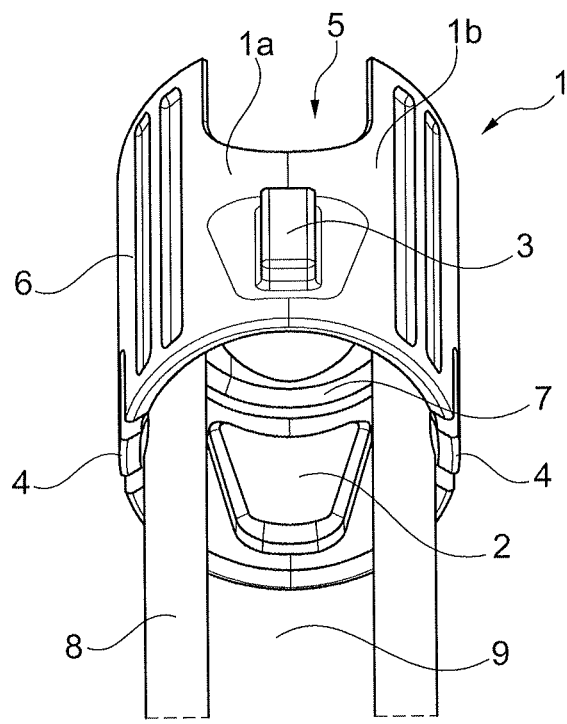
FIG. 6 is a detail view of a locking/securing sleeve according to the invention, placed on a pedicle screw comprising extended legs.

FIG. 6 shows in a detail view how the legs 8 are placed in the locking sleeve. The conical groove blocks 2 are placed between the legs 8 of the pedicle screw in spreading manner and thus keep the passage 9 between the legs 8 open. Here, the legs 8 rest on the locking sleeve 1 at the lateral face and extend so as to be parallel to each other. The stop ring 7 rests on the upper edges of the legs 8 in each case and defines the accommodation depth of the legs 8 in the locking sleeve 1. In this arrangement, the stop ring 7 does not protrude into the passage 9 defined by the legs 8.

Figure 7:
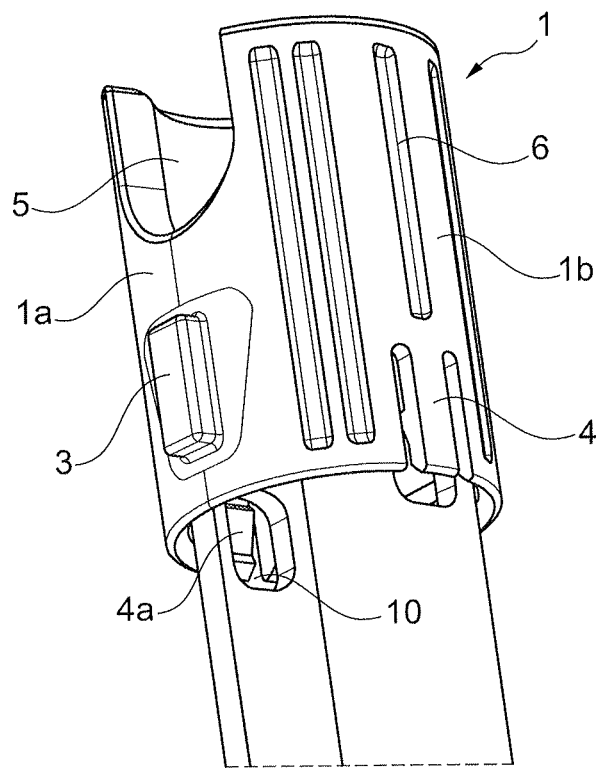
FIG. 7 is a detail view of a locking/securing sleeve according to the invention, placed on a pedicle screw comprising extended legs, seen from another point of view than that in FIG. 6.

FIG. 7 shows in a detail view how the latching arms 4 of the locking sleeve 1 each engage an elongated hole 10 in one of the legs 8 and in this way prevent the locking sleeve from being undesirably slipped off from the legs 8. The latching arms 4 can be elastically deformed in radial direction and comprise a respective protrusion 4a on their side facing the inner side of the locking sleeve. If the legs 8 are about to be inserted into the locking sleeve 1, the latching arms 4 comprising the protrusions 4a are pushed outward in elastic fashion until the latching arms 4 meet a respective elongated hole 10 of a leg 8 and latch in place therein. If the latching arms 4 are latched in place in the elongated holes 4a, a movement of the locking sleeve 1 contrary to the direction of inserting the legs 8 is prevented by the protrusion 4a of each latching arm 4, the former radially protruding into an elongated hole 10. Due to the cooperation between the stop ring 7 defining the position of the legs 8 in the locking sleeve 1 in the direction of inserting, the latching arms 4 defining the position of the legs 8 in the locking sleeve 1 contrary to the direction of inserting, and the groove blocks defining the position of the legs 8 in the circumferential direction of the locking sleeve 1 and preventing a rotation of the legs 8 in the circumferential direction of the locking sleeve 1, the position of the legs 8 in the locking sleeve 1 can be determinedly defined in all directions. Due to the special design of the locking sleeve 1, there will be no undercuts or dead areas, so that the locking sleeve 1 can be easily cleaned.

Figure 8:
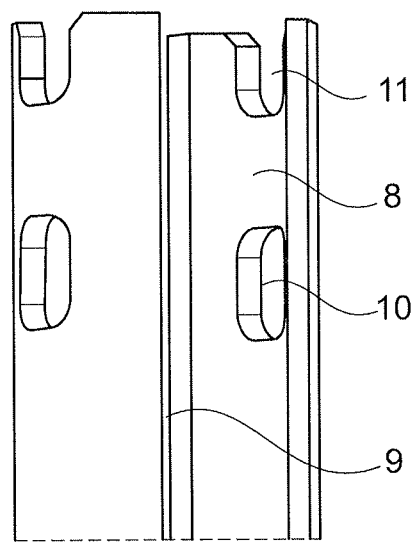
FIG. 8 is a detail view of the legs of a pedicle screw on which a locking/securing sleeve according to the invention can be placed.

FIG. 8 is a detail view of two legs 8 each comprising an elongated hole 10 for receiving a latching arm 4. Further, the ends of the legs 8 facing away from the pedicle screw are each provided with a groove 11 which is aligned with the elongated hole 10 of the respective leg 8.

Figure 9:
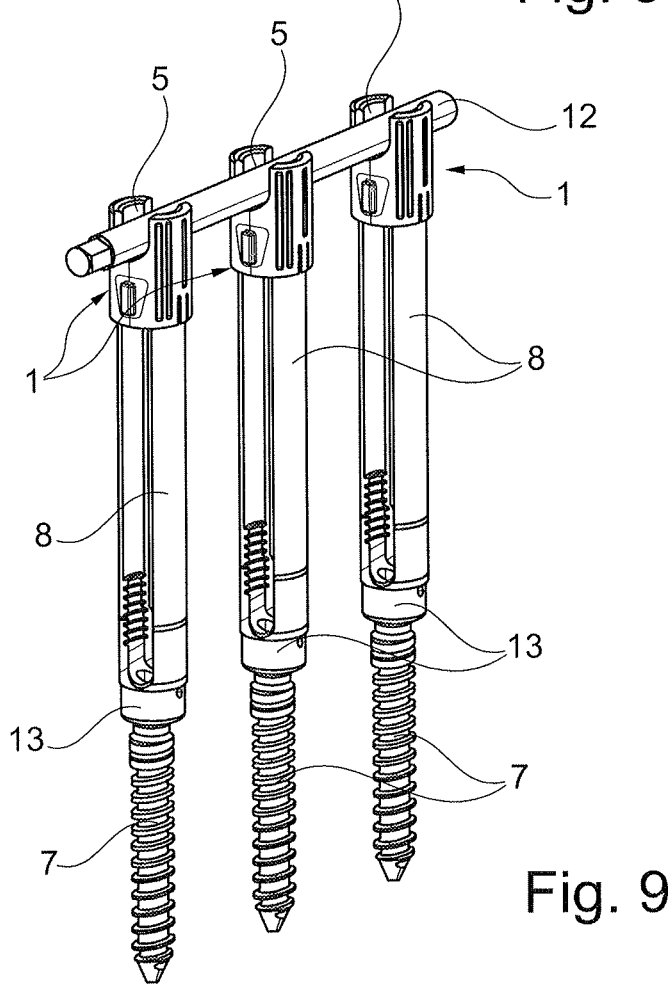
FIG. 9 shows the mutual alignment of several pedicle screws comprising extended legs and locking/securing sleeves according to the invention placed on the legs, said alignment brought about by a correction rod.

As shown in FIG. 9, the locking sleeve 1 has the additional function of mutually aligning the legs 8 of several pedicle screws 7, in addition to its function of locking the extended legs 8 of a pedicle screw 7. To this end, a correction rod 12 is placed in the alignment grooves 5 of several locking sleeves 1 each placed on two legs 8 of a pedicle screw 7. Thus, the correction rod is spaced from the tulip heads 13 of the pedicle screws 7 by the amount of the length of the legs 8. Accordingly, the mutual alignment of several pedicle screws 7 can be carried out in minimally invasive fashion and with minimum tissue damage.

The invention claimed is:

1. A locking sleeve for a pedicle screw comprising:
a first end;
a second end opposite the first end;
a first groove block on an inner side of the locking sleeve;
a second groove block on the inner side of the locking sleeve, the second groove block diametrically opposed to the first groove block;
a first alignment groove on the second end of the locking sleeve, the first alignment groove axially aligned with the first groove block;
a second alignment groove on the second end of the locking sleeve, the second alignment groove diametrically opposed to the first alignment groove and axially aligned with the second groove block; and
a stop ring or stop protrusion provided on the inner side of the locking sleeve;
wherein, the first groove block and the second groove block are adapted to be inserted between legs of the pedicle screw for defining a fixed distance between the legs,
wherein at least one of the first groove block and the second groove block conically tapers towards the first end of the locking sleeve, contrary to a direction of inserting the legs of the pedicle screw into the locking sleeve, and
wherein the stop ring or stop protrusion is adapted to rest on an axial upper edge of the legs and to limit the accommodation depth of the legs into the locking sleeve.

2. The locking sleeve according to claim 1, wherein a radial extension of the stop ring or stop protrusion into an inner circumference of the locking sleeve is limited by an inner circumference of a passage defined by the legs of the pedicle screw.

3. The locking sleeve according to claim 1, wherein a radial extension of the first and second groove blocks into an inner circumference of the locking sleeve corresponds at most to a radial extension of the stop ring or stop protrusion into the inner circumference of the locking sleeve.

4. The locking sleeve according to claim 1, wherein each of the first alignment groove and the second alignment groove faces away from the pedicle screw and serves for receiving a rod for aligning legs of several pedicle screws with respect to one another.

5. The locking sleeve according to claim 1, further comprising at least one restraining element on the first end of the locking sleeve facing the pedicle screw for preventing an undesired stripping of the locking sleeve from the legs contrary to the direction of inserting the legs into the locking sleeve.

6. The locking sleeve according to claim 5, wherein the at least one restraining element is formed as an elastically deformable latching arm preventing a movement of at least one of the legs contrary to the direction of inserting said at least one of the legs in the locking sleeve by latching in place in a corresponding elongated hole in said at least one of the legs.

7. The locking sleeve according to claim 1, wherein the locking sleeve consists of two half sleeves which are firmly connected to each other.

8. The locking sleeve according to claim 1, wherein the locking sleeve is manufactured in one piece.

9. A vertebral reposition system comprising at least one pedicle screw comprising a screw shaft and a tulip having extended tulip legs, the vertebral reposition system comprising a locking sleeve according to claim 1.

* * * * *